United States Patent [19]

Ryu et al.

[11] 4,343,747

[45] Aug. 10, 1982

[54] PREPARATION OF QUATERNARY AMMONIUM THIOMOLYBDATES

[75] Inventors: Yumi P. Ryu, Murrysville; Gary M. Singerman, Monroeville; James R. Anglin, Gibsonia, all of Pa.

[73] Assignee: Gulf Research & Development Company, Pittsburgh, Pa.

[21] Appl. No.: 213,676

[22] Filed: Dec. 5, 1980

[51] Int. Cl.$^3$ .............................................. C07F 11/00
[52] U.S. Cl. .................................................. 260/429 R
[58] Field of Search .................................... 260/429 R

[56] References Cited

U.S. PATENT DOCUMENTS 2,909,541 10/1959 Hugel .............................. 260/429 R
3,489,775 1/1970 de Roch et al. ............ 260/429 R X

OTHER PUBLICATIONS

Krause et al. JACS 47, 1689–1694, (1925).

Primary Examiner—Helen M. S. Sneed
Attorney, Agent, or Firm—Deane E. Keith; Forrest D. Stine; Donald L. Rose

[57] ABSTRACT

Quaternary ammonium thiomolybdates are prepared in a two-phase reaction system by contacting an aqueous solution of a thiomolybdate salt with a solution of a quaternary ammonium salt in a water-immiscible organic solvent. For example, mixing a solution of dicocodimethylammonium chloride in toluene with an aqueous solution of potassium thiomolybdate results in a toluene solution containing dicocodimethylammonium thiomolybdate.

10 Claims, No Drawings

PREPARATION OF QUATERNARY AMMONIUM THIOMOLYBDATES

SUMMARY OF THE INVENTION

This invention relates to a two-phase process for preparing certain quaternary ammonium thiomolybdates from certain, preferably water-insoluble, quaternary ammonium salts and water-soluble thiomolybdate salts. The quaternary ammonium salt is dissolved in a water-immiscible organic solvent, such as toluene or methylene chloride, and is agitated with an aqueous solution of a thiomolybdate salt. The resulting quaternary ammonium thiomolybdate is recovered from the organic solvent.

DETAILED DESCRIPTION OF THE INVENTION

The preparation of thiomolybdates of certain nitrogen bases in an aqueous solution is described in U.S. Pat. No. 2,909,541 by a process in which the nitrogen base and sodium thiomolybdate are reacted in the aqueous solution. However, we have found that certain tetra(hydrocarbon-substituted)quaternary ammonium salts are not water-soluble or are only slightly water-soluble and therefore cannot be effectively reacted in an aqueous solution. According to our invention we have discovered that a water-insoluble quaternary ammonium salt can be reacted with a water-soluble thiomolybdate salt in a two-phase system. In this reaction system the water-insoluble quaternary ammonium salt is dissolved in a suitable water-immiscible organic solvent and this solution is contacted and reacted with an aqueous solution of a suitable thiomolybdate salt. In this two-phase reaction system the novel quaternary ammonium thiomolybdate reaction product is in the organic solution while the by-product salt is in the aqueous solution.

The water-soluble thiomolybdate salts which are used in our process include the alkali metal thiomolybdates such as lithium thiomolybdate, sodium thiomolybdate, potassium thiomolybdate, rubidium thiomolybdate and cesium thiomolybdate. Other water-soluble thiomolybdates are also useful including ammonium thiomolybdate, thallium thiomolybdate and the like. These thiomolybdate salts, which are essentially insoluble in the organic solvents used herein, can be prepared by treating an aqueous alkaline solution of the corresponding molybdate salt with hydrogen sulfide. For example, potassium thiomolybdate is prepared by introducing hydrogen sulfide into an aqueous solution of potassium molybdate and potassium hydroxide.

The quaternary ammonium salts which are reacted as an organic solution with the aqueous solution of the thiomolybdate salt in the two-phase reaction according to our invention are defined by the following formula:

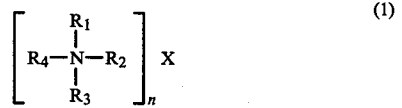

(1)

where $R_1$, $R_2$ and $R_3$ are independently selected from alkyl and alkenyl having from 1 to about 30 carbon atoms, preferably 1 to about 20 carbon atoms; $R_4$ is selected from alkyl and alkenyl having from about 5 to about 30 carbon atoms, preferably about 5 to about 20 carbon atoms, and benzyl; the total number of carbon atoms in $R_1$, $R_2$, $R_3$ and $R_4$ being at least about 20, preferably at least about 25 and no higher than about 80, preferably no higher than about 60 carbon atoms; n is the valence of X; and X is selected from chlorine, bromine, iodine, sulfate, hydrogen sulfate, lower alkyl sulfate, and the like.

Quaternary ammonium salts containing a mixture of alkyl and alkenyl groups of different carbon numbers can be derived from a mixture of naturally occurring fatty acids. Therefore, the number of carbon atoms for each R group in the above formula refers to the average number of carbon atoms when a mixture of hydrocarbon groups is used in its preparation.

Examples of suitable quaternary ammonium salts which can be reacted in accordance with our invention include
  tetrapentylammonium hydrogen sulfate,
  tetraheptylammonium methyl sulfate,
  didodecyldimethylammonium bromide,
  trioctylmethylammonium sulfate,
  dicocodimethylammonium chloride,
  ditallowdimethylammonium chloride,
  distearyldimethylammonium bromide,
  bis(hydrogenated-tallow)dimethylammonium sulfate,
  octadecyltrimethylammonium bromide,
  soyatrimethylammonium chloride,
  tallowtrimethylammonium chloride,
  tris(hydrogenated-tallow)methylammonium chloride,
  disoyadimethylammonium chloride,
  stearylbenzyldimethylammonium chloride,
  dodecylbenzyldimethylammonium bromide,
  dioctadecyldimethylammonium chloride and the like.

The two-phase process of our invention is most suitable and desirable when the quaternary ammonium salt is substantially soluble in the organic solvent and substantially insoluble in water. However, the process is also useful if the quaternary ammonium salt is somewhat soluble in water provided that it is substantially more soluble in the organic solvent. For this reason the useful quaternary ammonium salt can be defined broadly as having a solubility in the organic solvent of at least about five times, preferably at least about ten times its solubility in water at the reaction temperature. And most preferably the quaternary ammonium salt is essentially insoluble in water. In general, the solubility of the quaternary ammonium salt in water decreases and its solubility in the organic solvent increases as the total number of carbon atoms increases. Most of the quaternary ammonium salts defined by formula (1) are essentially insoluble in water, particularly when the total number of carbon atoms is at least about 25.

The solubility of these quaternary ammonium salts in water depends both on the specific hydrocarbon substituents and on the specific anion. The solubility of these salts in an organic solvent also depends on these two factors as well as on the specific solvent involved. This is illustrated in Table I which compares the various solubilities of tetraethylammonium and tetrabutylammonium salts in water, toluene and methylene chloride at about 20° C.

TABLE I

| Hydrocarbon | Anion | Solubility, g/100ml of solvent | | |
|---|---|---|---|---|
| | | Water | Toluene | Methylene chloride |
| tetraethyl | Br | >100 | 0 | 14 |
| tetrabutyl | Cl | >100 | 20 | 50 |

TABLE I-continued

| Hydrocarbon | Anion | Solubility, g/100ml of solvent | | |
|---|---|---|---|---|
| | | Water | Toluene | Methylene chloride |
| tetrabutyl | Br | >100 | 0.3 | >100 |
| tetrabutyl | I | 0 | 0 | >100 |
| tetrabutyl | HSO₄ | >100 | 0 | >100 |

This table suggests the criticality of the nature of hydrocarbon substituents, the criticality of the anion and the criticality of the solvent on the suitability of the present two-phase process, particularly with respect to quaternary ammonium salts containing a relatively low total number of carbon atoms. In the above table only tetrabutylammonium iodide in methylene chloride could be effectively utilized in a two-phase process as described herein. But this would be economically impractical since the use of tetrabutylammonium chloride could be carried out very conveniently and economically in a single-phase aqueous solution.

This water-immiscible solution containing the quaternary ammonium salt is mixed with an aqueous solution of the thiomolybdate salt. The product of this reaction, which is dissolved in the organic solvent, is a quaternary ammonium thiomolybdate having the general formula

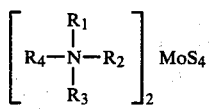 (2)

in which $R_1$, $R_2$, $R_3$ and $R_4$ are as defined above under formula (1).

Suitable water-immiscible organic solvents for the water-insoluble quaternary ammonium salts include aliphatic hydrocarbons having from about five to about 20 carbon atoms, preferably about five to about ten carbon atoms, such as pentane, hexane, heptane, decane, hexadecane, and the like; aromatic hydrocarbons and halogenated aromatic hydrocarbons having from six to about eight carbon atoms, such as benzene, toluene, xylene, ethylbenzene, chlorobenzene, dichlorobenzene, benzyl chloride, and the like; halogenated aliphatic hydrocarbons having from one to about two carbon atoms, such as methylene chloride, chloroform, carbon tetrachloride, ethylene dichloride, ethylidene chloride, and the like. The suitable organic solvents also include the alkyl esters of aliphatic carboxylic acids having from about four to about seven carbon atoms, including ethyl acetate, butyl acetate, amyl acetate, methyl propionate, and the like; aliphatic ketones having from about five to about ten carbon atoms including isobutylmethyl ketone, diisobutyl ketone, and the like; and alkyl ethers having from about four to about eight carbon atoms such as diethyl ether, ethylpropyl ether, diisopropyl ether, and the like. Mixtures of the above organic solvents can also be used.

The initial concentration of the quaternary ammonium salt in the organic solvent prior to the reaction can broadly range from about one to about 30 weight percent, but preferably it will range from about five to about 20 weight percent. The initial concentration of the thiomolybdate salt in the aqueous solution can be between about one and about 30 weight percent, but the reaction is preferably conducted at a concentration between about three and about 20 weight percent.

The reaction is carried out by contacting the organic solution of the quaternary ammonium salt with the aqueous solution of the thiomolybdate salt. Since temperature is not a critical factor in this reaction, it is convenient to carry out the reaction at about room temperature (20°-25° C.). Although we have not studied the precise mechanism for this two-phase reaction, we believe that the desired reaction takes place at the interface between the organic phase and the aqueous phase. We find that stirring the reactant mixture, preferably with sufficient agitation to cause a substantial increase in the area of contact between the two phases, facilitates the reaction.

At the completion of the reaction the desired water-insoluble quaternary ammonium thiomolybdate is in the organic solution and the by-product salt, such as potassium sulfate or sodium chloride, is in the aqueous solution. This thiomolybdate reaction product is recovered by separating the two liquid phases, such as by decantation or by using a separating funnel, and evaporating or distilling off the organic solvent. The resulting dark red thiomolybdate reaction product is a waxy, semi-solid to solid material. This two-phase reaction system conveniently avoids the incorporation of difficult-to-remove water and by-product salt into this waxy, semi-solid or solid product, which would occur if a product having these physical characteristics were precipitated from a single phase aqueous solution. The relatively pure quaternary ammonium thiomolybdate product is stable up to a temperature of about 170° to about 200° C. depending on the specific compound.

It is preferred to carry out the reaction using quantities ranging from a stoichiometric quantity, that is a ratio of two mols of the quaternary ammonium salt for each mol of the thiomolybdate salt, to a slight stoichiometric excess such as a five to ten percent excess of the thiomolybdate salt. When the reaction is carried out in this range, two desirable objectives are accomplished. First, the most efficient utilization of reactants is accomplished. And second, the quaternary ammonium salt in the organic phase is fully reacted thereby eliminating it as a potential impurity in the quaternary ammonium thiomolybdate product. However, the reaction can be carried out within a much wider range of proportions at a sacrifice of these benefits.

The naturally occurring fatty acids are an excellent and convenient source of the higher molecular weight alkyl and alkenyl groups in the quaternary ammonium salt used herein. As used herein, the term alkenyl includes mono-, di- and tri-olefinic groups. These fatty acids can be converted to the corresponding alkenyl group and saturated, if desired, by conventional hydrogenation procedures. For example, oleic acid can be converted to octadecenyl and this can be hydrogenated to octadecyl. Since the naturally occurring fats comprise mixtures of two and generally more carbon chains of different lengths, the resulting quaternary compounds contain the alkenyl and alkyl groups in the same relative proportion as the precursor acids occur in the fat. The relative proportion of alkyl and alkenyl groups of various chain lengths that are derived from different natural sources referred to herein is set out in the following table in which coco is derived from coconut oil, tallow and stearyl are derived from beef fat and soya is derived from soya bean oil.

TABLE II

| chain length | coco | tallow | stearyl | soya |
|---|---|---|---|---|
| $C_8$ | 5 | — | — | — |
| $C_{10}$ | 8 | — | — | — |
| $C_{12}$ | 50 | — | — | — |
| $C_{14}$ | 18 | 5 | — | — |
| $C_{16}$ | 8 | 30 | 8 | 15 |
| $C_{17}$ | — | — | 1 | — |
| $C_{18}$ | 11 | 65 | 91 | 85 |

DESCRIPTION OF PREFERRED EMBODIMENTS

In carrying out the following experiments we found that the desired quaternary ammonium thiomolybdate product was recovered in quantitative yields based on the reactant quaternary ammonium salt, less minor processing losses, when relatively large quantities of reactants were utilized, e.g. Examples 1 and 7. When relatively minute amounts of reactants were used, less than quantitative yields of product were recovered due to significant processing losses. Nevertheless, quantitative reaction was indicated from the loss of the red color of the aqueous solution caused by the disappearance of the potassium thiomolybdate in those examples containing a 2:1 molar ratio of the quaternary ammonium salt to the potassium thiomolybdate, e.g. Examples 3, 6 and 8.

EXAMPLE 1

A 360 g quantity of a commercial mixture containing 75 percent dicocodimethylammonium chloride (0.615 mol) and 25 percent isopropanol was dissolved in one liter of toluene and this solution was stirred with an aqueous solution containing 102 g (0.337 mol) of potassium thiomolybdate in one liter of water at room temperature for 30 minutes. After separating out the dark red toluene layer and water washing it, the toluene was removed under reduced pressure. A quantitative yield of semi-solid, dark red dicocodimethylammonium thiomolybdate was obtained. Analysis of the product for thiomolybdate ion by infrared spectroscopy showed 460/cm and by ultraviolet-visible spectroscopy in toluene showed a band at 470 nm. The calculated elemental analysis for dicocodimethylammonium thiomolybdate was N, 2.7%; S, 12.2% and Mo, 9.15%. The actual elemental analysis was N, 2.63%; S, 12.44% and Mo, 9.3%.

EXAMPLE 2

A solution containing 1.77 g (3 mmol) of distearyldimethylammonium chloride and seven percent isopropanol was dissolved in 30 ml of methylene chloride. This organic solution was mixed with an aqueous solution containing 0.5 g (1.6 mmol) of potassium thiomolybdate in 10 ml of water. After 15 minutes, the stirring was stopped and the solutions were permitted to separate. The bottom methylene chloride solution was separated from the aqueous layer and was dried over anhydrous magnesium sulfate. The methylene chloride was removed under reduced pressure and 0.9 g of dark red, solid distearyldimethylammonium thiomolybdate was obtained.

EXAMPLE 3

Dioctadecyldimethylammonium thiomolybdate was prepared by mixing 6.31 g (10 mmol) of dioctadecyldimethylammonium chloride in 100 ml of toluene with 1.5 g (5 mmol) of potassium thiomolybdate in 50 ml of water. The resulting dioctadecyldimethylammonium thiomolybdate (3.8 g) was a dark red solid material.

EXAMPLE 4

A dialkyl($C_{12-16}$)dimethylammonium thiomolybdate was prepared by dissolving a solution containing 4.1 g (9 mmol) of a dialkyl($C_{12-16}$)dimethylammonium chloride and 32 percent isopropanol in 100 ml of toluene. This solution was agitated with a solution containing 1.5 g (5 mmol) of potassium thiomolybdate in 50 ml of water. The resulting dialkyl($C_{12-16}$)dimethylammonium thiommolybdate (4.5 g), dark red in color, was a semi-solid material.

EXAMPLE 5

Bis(hydrogenated-tallow)dimethylammonium thiomolybdate was prepared from 5.1 g (9 mmol) of the corresponding quaternary ammonium chloride and 1.5 g of potassium thiomolybdate using the same solvents in the same quantities as used in Example 4. The resulting thiomolybdate product (5 g) was also a dark red, semi-solid material.

EXAMPLE 6

Tris(hydrogenated-tallow)methylammonium thiomolybdate was prepared by dissolving a solution containing 5.25 g (6 mmol) of tris(hydrogenated-tallow)methylammonium chloride and 50 percent isopropanol in 200 ml of toluene. This solution was agitated with a solution containing 1.0 g (3 mmol) of potassium thiomolybdate in 30 ml of water. The resulting tris(hydrogenated-tallow)methylammonium thiomolybdate product (5 g) was a dark red, semi-solid material.

EXAMPLE 7

A solution containing 120 g (0.297 mol) of trioctylmethylammonium chloride in 800 ml of toluene was vigorously stirred for 30 minutes with a solution containing 51 g (0.168 mol) of potassium thiomolybdate in 500 ml of water. Following the reaction the toluene layer was separated and the toluene was removed at reduced pressure. There was a quantitative recovery of the red viscous trioctylmethylammonium thiomolybdate.

EXAMPLE 8

A solution containing 3.2 g (6 mmol) of tetraheptylammonium iodide in 50 ml of methylene chloride was vigorously mixed for about 15 minutes with an aqueous solution consisting of 1.0 g (3 mmol) of potassium thiomolybdate and 30 ml of water. After the completion of the reaction, the tetraheptylammonium thiomolybdate and methylene chloride layer was separated from the aqueous layer and 2.7 g of tetraheptylammonium thiomolybdate, a brick-red solid product, was recovered by removing the methylene chloride at reduced pressure.

EXAMPLE 9

A solution containing 6.4 g (18 mmol) of a alkyl($C_{12-16}$)benzyldimethylammonium chloride and 20 percent isopropanol is dissolved in 100 g of methylene chloride. This solution is vigorously stirred with an aqueous solution containing 3.0 g (10 mmol) of potassium thiomolybdate in 50 ml of water for about 15 minutes. A dark red solid product consisting of alkyl($C_{12-16}$)-benzyldimethylammonium thiomolybdate is produced in quantitative yield based on the quaternary ammonium salt.

EXAMPLE 10

A solution containing 3.9 g (9 mmol) of a 1:1 molar mixture of tallowtrimethylammonium chloride and dicocodimethylammonium chloride and 50 percent isopropanol was dissolved in 100 ml of toluene. This solution was vigorously stirred with a solution containing 1.5 g of potassium thiomolybdate in 50 ml of water for about 15 minutes. The organic layer was separated from the aqueous layer and the organic solvent removed at reduced pressure. A dark red semi-solid mixture (7 g) of tallowtrimethylammonium thiomolybdate and dicocodimethylammonium thiomolybdate was recovered.

EXAMPLE 11

Example 10 was repeated using a 1:1 molar mixture of soyatrimethylammonium chloride and dicocodimethylammonium chloride and the same quantities. A dark red semi-solid mixture (7.4 g) of soyatrimethylammonium thiomolybdate and dicocodimethylammonium thiomolybdate was recovered.

Various members of the compounds prepared by the process described herein find use as additives in motor oils or greases to enhance the antifriction and EP characteristics. For example, the presence of one percent trioctylmethylammonium thiomolybdate in a diurea-type grease such as described in U.S. Pat. No. 4,065,395 increased the maximum load without seizure, welding or scoring as measured by ASTM D2509 from 30 lb/ft$^2$ without the additive to 60 lb/ft$^2$ with the additive.

It is to be understood that the above disclosure is by way of specific example and that numerous modifications and variations are available to those of ordinary skill in the art without departing from the true spirit and scope of the invention.

We claim:

1. The method of making quaternary ammonium thiomolybdates in a two-phase reaction system which comprises contacting an aqueous solution of a water-soluble thiomolybdate salt with a solution of a quaternary ammonium salt having the formula

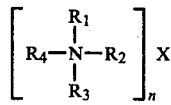

where $R_1$, $R_2$ and $R_3$ are independently selected from alkyl or alkenyl having from one to about 30 carbon atoms; $R_4$ is selected from alkyl or alkenyl having from about 5 to about 30 carbon atoms, and benzyl; the total number of carbon atoms in $R_1$, $R_2$, $R_3$ and $R_4$ is between about 20 and about 80; n is the valence of X; and X is selected from chlorine, bromine, iodine, sulfate, hydrogen sulfate and lower alkyl sulfate; in a water-immiscible organic solvent selected from aliphatic hydrocarbons having from about five to about 20 carbon atoms, halogenated aliphatic hydrocarbons having from about one to about two carbon atoms, aromatic hydrocarbons and halogenated aromatic hydrocarbons having from six to about eight carbon atoms, alkyl esters of aliphatic carboxylic acids having from about four to about seven carbon atoms, aliphatic ketones having from about five to about ten carbon atoms, alkyl ethers having from about four to about eight carbon atoms, and mixtures thereof; wherein the solubility of said quaternary ammonium salt in said organic solvent is at least about five times its solubility in water; and recovering the quaternary ammonium thiomolybdate produced thereby in the said organic solvent and the by-product salt in the aqueous solution.

2. The method of making quaternary ammonium thiomolybdates in accordance with claim 1 wherein $R_1$, $R_2$ and $R_3$ have from one to about 20 carbon atoms, $R_4$ has from about 12 to about 20 carbon atoms, and the total number of carbon atoms in $R_1$, $R_2$, $R_3$ and $R_4$ is between about 25 and about 60.

3. The method of making quaternary ammonium thiomolybdates in accordance with claim 1 wherein the water-soluble thiomolybdate salt is selected from lithium, sodium, potassium, rubidium, cesium, thallium and ammonium thiomolybdate.

4. The method of making quaternary ammonium thiomolybdates in accordance with claim 2 wherein $R_1$, $R_2$, $R_3$ and $R_4$ are the same.

5. The method of making quaternary ammonium thiomolybdates in accordance with claim 2 wherein $R_1$ and $R_2$ are methyl and $R_3$ has from about 12 to about 20 carbon atoms.

6. The method of making quaternary ammonium thiomolybdates in accordance with claim 2 wherein $R_1$ is methyl and $R_2$ and $R_3$ have from about 12 to about 20 carbon atoms.

7. The method of making quaternary ammonium thiomolybdates in accordance with claim 2 wherein said quaternary ammonium salt is essentially insoluble in water.

8. The method of making quaternary ammonium thiomolybdates in accordance with claim 1 wherein the ratio of the quaternary ammonium salt to the water-soluble thiomolybdate salt is between a mol ratio of about 2:1 and about a ten percent stoichiometric excess of the water-soluble thiomolybdate salt.

9. The method of making quaternary ammonium thiomolybdates in accordance with claim 1 wherein the solubility of said quaternary ammonium salt in said organic solvent is at least about ten times its solubility in water.

10. The method of making quaternary ammonium thiomolybdates in accordance with claim 1 wherein said product quaternary ammonium thiomolybdate is recovered substantially free of water and by-product salt.

* * * * *